United States Patent [19]

Huth et al.

[11] Patent Number: 4,945,163

[45] Date of Patent: Jul. 31, 1990

[54] PROCESS FOR THE PREPARATION OF 4-ALKOXYALKYL β-CARBOLINES

[75] Inventors: Andreas Huth; Dieter Rahtz; Ralph Rohde; Ralph Schmiechen; Dieter Seidelmann, all of Berlin, Fed. Rep. of Germany

[73] Assignee: Schering Aktiengesellschaft, Berlin and Bergkamen, Fed. Rep. of Germany

[21] Appl. No.: 238,086

[22] Filed: Aug. 30, 1988

[30] Foreign Application Priority Data

Aug. 31, 1987 [DE] Fed. Rep. of Germany ....... 3729370

[51] Int. Cl.⁵ ................. C07D 471/14; A61K 31/435
[52] U.S. Cl. ........................ 546/85; 546/14; 546/86; 546/87
[58] Field of Search ........................ 546/85, 86, 87, 14

[56] References Cited

U.S. PATENT DOCUMENTS 4,435,403 3/1984 Braestrup et al. .................. 514/292

Primary Examiner—Alan L. Rotman
Attorney, Agent, or Firm—Millen, White & Zelano

[57] ABSTRACT

A process is disclosed for the preparation of 4-alkoxyalkyl β-carboline derivatives of general Formula I

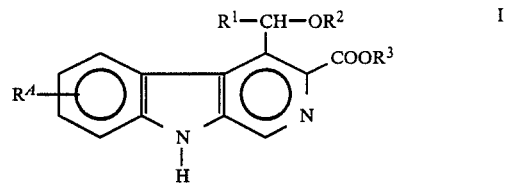

wherein
$R^1$ is hydrogen or methyl,
$R^2$ is an optionally substituted aliphatic hydrocarbon residue,
$R^3$ is lower alkyl, and
$R^4$ is hydrogen, halogen, $COOR^4$ or $OR^5$, $R^4$ meaning lower alkyl and $R^5$ meaning hydrogen, lower alkyl, cycloalkyl, or optionally substituted pheny, by reaction of a compound of Formula II in the presence of $AgBF_4$ with an alcohol of the formula $R^2OH$ wherein $R^2$ has the meanings given above.

19 Claims, No Drawings

PROCESS FOR THE PREPARATION OF 4-ALKOXYALKYL β-CARBOLINES

BACKGROUND OF THE INVENTION

The invention relates to a process for the preparation of 4-alkoxyalkyl β-carboline derivatives.

β-Carbolines substituted in the 4-position by an alkoxyalkyl group exhibit a very good binding affinity to the benzodiazepine receptors, as has been disclosed in earlier applications, for example in EP-A No. 54,507; 161,575; 234,173; 130,140.

In accordance with the previously known method, the alkoxyalkyl group is already introduced at a quite early reaction step so that, for the production of alkoxyalkylated compounds, the entire β-carboline synthesis must be run through. This synthesis is also made difficult by the fact that the aldehydes utilized must themselves be prepared in syntheses that are difficult to handle. Merely the methoxyacetaldehyde can be obtained commercially.

Therefore, the problem to be resolved resides in developing a widely applicable process for the preparation of 4-alkoxyalkyl β-carbolines permitting the introduction of the alkoxyalkyl residue into diverse β-carbolines in a simple way with high yields and in the presence of nontoxic compounds.

Etherification of the corresponding haloalkyl compound with alcoholates, which is an obvious procedure, leads primarily to undesired condensation products and has been accomplished only with the iodoalkyl compound, less readily accessible, and then also merely with ethanol in a poor yield.

However, when adding to the alcoholic solution of the β-carboline silver tetrafluoroborate as the catalyst, the etherification is accomplished with a very good yield and purity of the product in a simple way with broad range of variation and without expensive separation operations or addition of toxic reaction additives.

The O-alkylation in the presence of silver salts has been reported on, for example, in the Merck Schuchardt O15 Info 84-4 reference. It can be seen from the latter that rearrangements take place frequently when using silver tetrafluoroborate.

It was therefore surprising that, under the claimed reaction conditions, etherification with aliphatic alcohols is achieved in one reaction step in good yields of 4-haloalkyl β-carboline derivatives, wherein also sterically hindered alcohols, such as tert-butanol, and readily rearranging alcohols, such as cyclobutanol and cyclopropylmethanol can also be reacted.

SUMMARY OF THE INVENTION

The invention concerns a process for the preparation of 4-alkoxyalkyl β-carboline derivatives of general Formula I

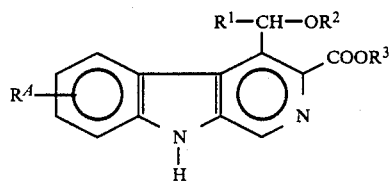

wherein
$R^1$ is hydrogen or methyl,
$R^2$ is an optionally substituted aliphatic hydrocarbon residue,
$R^3$ is lower alkyl, and
$R^4$ is hydrogen, halogen, $COOR^4$ or $OR^5$,
  $R^4$ meaning lower alkyl and
  $R^5$ meaning hydrogen, lower alkyl, cycloalkyl, or optionally substituted phenyl, characterized by reacting a compound of general Formula II

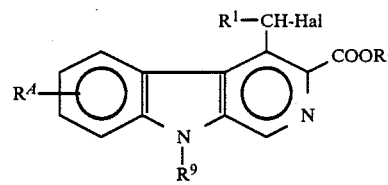

wherein
$R^1$ and $R^3$ have the meanings given above and
$R^4$ is hydrogen, halogen, $COOR^4$ or $OR^5$,
  R4 meaning lower alkyl and
  R5 meaning hydrogen, lower alkyl, lower acyl, cycloalkyl, or optionally substituted phenyl, and
Hal is halogen and
$R^9$ is a blocking group,
in the presence of $AgBF_4$ with an alcohol of the formula $R_2OH$ wherein $R_2$ has the meanings indicated above, and optionally splitting off the blocking group.

Suitable as the aliphatic hydrocarbon residue $R^2$ are saturated, unsaturated, straight-chain and branched, optionally substituted groups, of preferably 1-6 carbon atoms, and furthermore cycloalkyl and cycloalkylalkyl groups of preferably 3-7 carbon atoms which can be substituted.

Suitable saturated groups are, for example, methyl, ethyl, propyl, isopropyl, butyl, isobutyl, sec-butyl, tert-butyl, pentyl, 2-methylbutyl, 2,2-dimethylpropyl, and hexyl, and other isomers.

As the unsaturated groups, the following alkenes and alkynyls of 3-5 carbon atoms are preferred: 2-propenyl, 3-methyl-2-propenyl, 2-propynyl, methallyl and other isomer.

Suitable substituents are halogens, especially fluorine and chlorine, and also $C_{1-2}$-alkoxy groups. The substituents may be the same or different and typically number 1-3.

In case the hydrocarbon residue $R^2$ means a cycloalkyl group, then preferred examples that can be cited are cyclopropyl, cyclobutyl, cyclopentyl, cyclohexyl, and cycloheptyl.

As the cycloalkylalkyl group $R^2$, suitable are, for example, the cyclopropylmethyl, cyclopropylethyl, and cyclopentylmethyl groups.

Lower alkyl groups $R^3$, $R^4$ and $R^5$ are, for example, the above-mentioned alkyl residues of 1-4 carbon atoms. $R^5$ can also be cycloalkyl, hydrogen or optionally substituted phenyl.

If $R^5$ is a substituted phenyl residue, then the residues mentioned in EP-A No. 214,173 can be utilized, preferred substituents being halogen, i.e. chlorine, bromine, iodine and fluorine, lower alkyl and lower alkoxy with lower meaning 1-4 carbon atoms. The phenyl group can typically contain 1-3 substituents.

Suitable cycloalkyl residues $R^5$ are the cycloalkyl residues recited for $R^2$.

Suitable as the lower acyl residue $R^5$ are those from hydrocarbon carboxylic acids of up to 4 carbon atoms.

In particular, the acetyl residue can be used which, during etherification, is split off in a saponification reaction.

The substituent $R^4$ can be located singly to doubly in the 5-, 6-, or 7-position on the β-carboline, with the 5- or 6-position being preferred.

The substituent $R^9$ represents customarily employed blocking groups, such as, for example, an acyl, arylsulfonyl or silyl group, such as the trialkylsilyl group and typically is one of the groups defined by $R^5$ and arylsulfonyl is typically benzenesulfonyl.

Suitable as the halogen are fluorine, chlorine, bromine, and iodine and, in the haloalkyl compound of general Formula II, especially bromine and chlorine.

The etherification of the compounds of general Formula II takes place at temperatures from room temperature up to the boiling temperature of the solvent and is generally finished after 1-3 hours.

Suitable solvents are the corresponding alcohols used as a reactant and also mixtures of the alcohols with hydrocarbons, ethers and chlorinated hydrocarbons.

Suitably, the process is carried out under an inert gas atmosphere, e.g. under nitrogen or argon.

Silver tetrafluoroborate is added as the catalyst in stoichiometric quantity or in a small excess to the reaction solution.

The blocking group is split off under the reaction conditions or can be split off subsequently in accordance with the usual methods, e.g. by treatment with bases, such as sodium or potassium alcoholate, or acids, such as a dilute mineral acid of trifluoroacetic acid in inert solvents, such as alcohols, hydrocarbons, and others, at room temperature.

The resultant compounds of general Formula I are all useful pharmaceuticals per se and also can be reacted, especially in case $R^4$=OH, according to conventional methods to from very highly effective pharmaceuticals (for example, EP-A No. 130,140; EP-A No. 237,467; EP-A No. 239,667).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

The entire texts of all applications, patents and publications cited above and below, and of corresponding application(s), including German P. No. 37 29 510.2 are hereby incorporated by reference.

EXAMPLES

The starting compounds are produced in a simple way, for example according to the method described herein below:

9-Acetyl-4-bromomethyl-β-carboline-3-carboxylic Acid Ethyl Ester (G. Neef et al., Het. 20(7) : 1295 [1983])

10 g (33.8 mmol) of 9-acetyl-4-methyl-β-carboline-3carboxylic acid ethyl ester is combined in 500 ml of carbon tetrachloride with 12 g (67.4 mmol) of N-bromosuccinimide and one spatula tip of azobisisobutyronitril and heated to reflux for 1.5 hours while simultaneously exposing the reaction mixture to light. After cooling, the mixture is suctioned off from the succinimide, concentrated, and the residue is extracted by stirring with hot water and suctioned off. Yield: 10.64 g (84%) of 9-acetyl-4-bromomethyl-β-carboline-β-carboxylic acid ethyl ester, mp 188°–189° C.

Analogously, the 4-bromomethyl compounds are produced from the compounds disclosed in EP-A No. 54,507; 128,415; 161,575; and 234,173.

Examples that can be cited are:

9-acetyl-4-bromomethyl-5-isopropoxy-β-carboline-3-carboxylic acid ethyl ester in a 74.3% yield;

9-acetyl-5-acetoxy-4-bromomethyl-β-carboline-3-carboxylic acid ethyl ester in a 60% yield;

9-acetyl-4-bromoethyl-6-phenoxy-β-carboline-3-carboxylic acid ethyl ester in a 90% yield.

The following examples are to explain the process of this invention.

General Operating Procedure:

4-Methoxymethyl-β-carboline-3-carboxylic Acid Ethyl Ester

Under argon, 372 mg (1 mmol) of 4-bromomethyl-9-acetyl-β-carboline-3-carboxylic acid ethyl ester is heated to 50° C. in 20 ml of methanol and combine with 390 mg (2mmol) of silver tetrafluoroborate. The mixture is then refluxed for one hour. After allowing the mixture to stand overnight, it is suctioned off over kieselguhr and rinsed with methanol. After concentration of the filtrate, the mixture is distributed in methylene chloride and dilute aqueous ammonia, the aqueous phase is extracted twice by shaking with methylene chloride, and the collected organic phase is washed with water. After drying over silica, filtration, and concentration, the product is chromatographed over silica gel. Initially with toluene : glacial acetic acid : water = 10:10:1.

After combining and concentration of the corresponding fractions, the mixture is distributed in ethyl acetate/dilute ammonia.

Yield: 120 mg (42,3%) of 4-methoxymethyl-β-carboline-3-carboxylic acid ethyl ester, mp 104°–106° C.

The compounds set forth in the table are obtained analogously.

| $R^4$ | $R^1$ | $R^2$ | $R^3$ | Melting Point °C. |
|---|---|---|---|---|
| H | H | Me | Et | 104–106 |
| H | H | Et | Et | 126–129 |
| H | H | n-Prop | Et | 195–197 |
| H | H | n-But | Et | 103–105 |
| H | H | i-Prop | Et | 170–173 |
| H | H | tert-But | Et | 162–163 |
| H | H | Allyl | Et | 129–131 |
| H | H | $CH_2-CH_2-OCH_3$ | Et | 88–90 |
| H | H | $CH_2-CF_3$ | Et | 190–192 |
| H | $CH_3$ | Et | Et | 171–173 |
| H | H | Cyclobutyl | i-Prop | 204–205 |
| H | H | Cyclopropylmethyl | Et | 160–161 |
| OH | H | Prop | Et | 188–190 |
| Phenoxy | H | Prop | i-Prop | 171–172 |
| O-i-Prop | H | n-Prop | Et | 203–204 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification so of the invention to adapt it to various usages and conditions.

What is claimed is:

1. A process for the preparation of a 4-alkoxyalkyl β-carboline of Formula I

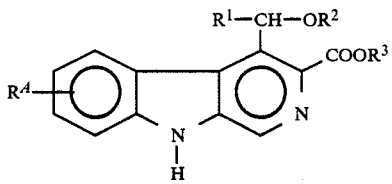

wherein
R$^1$ is hydrogen or methyl;
R$^2$ is a saturated or unsaturated, straight-chain or branched, aliphatic hydrocarbon residue containing 1–6 carbon atoms or a cycloalkyl or cycloalkylalkyl group containing 3–7 carbon atoms which can contain 1–3 substituents, said substituents being halogens or C$_{1-2}$-alkoxy groups;
R$^3$ is C$_{1-4}$-alkyl;
R$^A$ is hydrogen, halogen, COOR$^4$ or OR$^5$;
R$^4$ is C$_{1-4}$-alkyl;
R$^5$ is hydrogen, C$_{1-4}$-alkyl, C$_{3-7}$-cycloalkly, unsubstituted phenyl, or a substituted phenyl group containing 1-3 substituents selected from the group comprising chlorine, bromine, iodine, fluorine, C$_{1-4}$-alkyl and C$_{1-4}$-alkoxy;
comprising reacting a compound of general Formula II

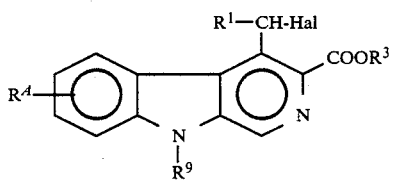

wherein
R$^1$, R$^3$, R$^4$, R$^5$ and R$^A$ have the meanings given above,
Hal is halogen, and
R$^9$ is an acyl, arylsulfonyl, or silyl group, in the presence of AgBF$_4$ with an alcohol of the formula R$^2$OH wherein R$^2$ has the meanings indicated above, and optionally splitting off the blocking group.

2. A process according to claim 1, wherein R$^2$ is a saturated, unsaturated, straight chain or branched group containing 1–6 carbon atoms.

3. A process according to claim 1, wherein R$^2$ is methyl, ethyl, propyl, isopropyl, butyl, isobutyl, sec-butyl, tert-butyl, pentyl, 2-methylbutyl, 2,2-dimethylpropyl and hexyl.

4. A process according to claim 2, wherein R$^2$ is 2-propenyl, 3-methyl, 2-propenyl, 2-propynyl, or methallyl.

5. A process according to claim 1, wherein R$^2$ is a cycloalkylalkyl group having 3–7 carbon atoms.

6. A process according to claim 5, wherein R$^2$ is cyclopropylmethyl, cyclopropylethyl or cyclopentylmethyl.

7. A process according to claim 1, wherein R$^2$ is a cycloalkyl group containing 3–7 carbon atoms.

8. A process according to claim 7, wherein R$^2$ is cyclopropyl, cyclobutyl, cyclopentyl, cyclohexyl or cycloheptyl.

9. A process according to claim 1, wherein R$^3$, R$^4$ and R$^5$ are C$_{1-4}$ alkyl residues, 10. A process according to claim 1, wherein R$^A$ is located singly or doubly in the 5-, 6- or 7-position.

11. A process according to claim 10, wherein R$^A$ is in the 5- or 6-position.

12. A process according to claim 1, wherein R$^5$ is a C$_{3-7}$ cycloalkyl residue.

13. A process according to claim 12, wherein R$^5$ is cyclopropyl, cyclobutyl, cyclopentyl, cyclohexyl, or cycloheptyl.

14. A process according to claim 1, wherein R$^5$ is a phenyl residue, substituted by halogen, C$_{1-4}$-alkyl or C$_{1-4}$-alkoxy.

15. A process according to claim 1, wherein R$^A$ is OH.

16. A process according to claim 1, wherein the reaction takes place in the range of room temperature to the boiling temperature of the solvent.

17. A process according to claim 1, wherein the reaction is carried out under an inert gas atmosphere.

18. A process according to claim 1, wherein the silver tetrafluoroborate is added in stoichiometric quantity or in a slight excess.

19. A process according to claim 1, wherein R$^9$ is split off with an acid or base.

* * * * *